(12) United States Patent
Hutchins et al.

(10) Patent No.: US 7,371,237 B2
(45) Date of Patent: *May 13, 2008

(54) STEERABLE SPHINCTEROTOME AND METHODS FOR CANNULATION, PAPILLOTOMY AND SPHINCTEROTOMY

(75) Inventors: John E. Hutchins, North Attleboro, MA (US); Mark L. Adams, Sandy, UT (US)

(73) Assignee: Scimed Life Systems, Inc., Maple Grove, MN (US)

( * ) Notice: Subject to any disclaimer, the term of this patent is extended or adjusted under 35 U.S.C. 154(b) by 629 days.

This patent is subject to a terminal disclaimer.

(21) Appl. No.: 10/651,992

(22) Filed: Sep. 2, 2003

(65) Prior Publication Data

US 2005/0192607 A1 Sep. 1, 2005

Related U.S. Application Data

(63) Continuation of application No. 09/928,655, filed on Aug. 14, 2001, now Pat. No. 6,676,659.

(60) Provisional application No. 60/224,981, filed on Aug. 14, 2000.

(51) Int. Cl.
*A61B 18/18* (2006.01)
*A61B 17/32* (2006.01)
*A61B 17/20* (2006.01)

(52) U.S. Cl. .................... 606/47; 606/167; 604/22

(58) Field of Classification Search ............... 606/39, 606/127, 128, 167, 170, 106, 108, 110, 113, 606/159, 45, 47; 604/22, 107–109, 523; 128/898; 600/137, 144, 146, 147
See application file for complete search history.

(56) References Cited

U.S. PATENT DOCUMENTS

| | | | |
|---|---|---|---|
| 5,327,905 A | * | 7/1994 | Avitall ........................ 606/45 |
| 5,599,300 A | | 2/1997 | Weaver et al. |
| 6,533,782 B2 | * | 3/2003 | Howell et al. ............... 606/47 |
| 6,676,659 B2 | * | 1/2004 | Hutchins et al. ............. 606/47 |
| 6,746,442 B2 | * | 6/2004 | Agro et al. ................. 604/523 |

* cited by examiner

*Primary Examiner*—Julian W. Woo
(74) *Attorney, Agent, or Firm*—Fulbright & Jaworski LLP

(57) ABSTRACT

The present invention relates to methods and devices for performing endoscopic cannulation, papillotomy and sphincterotomy and similar procedures. According to the present state of the art, endoscopic cannulation of the common bile duct and papillotomy and similar procedures are accomplished by advancing the device into an endoscope/duodenoscope so that the distal tip of the device exits the endoscope adjacent the sphincter muscles at the Papilla of Vater. The endoscope mechanisms are then manipulated to orient the distal tip of the device to the desired position for proper cannulation of the duct. Due to inconsistencies in, for example, the sphincterotome, anatomy, and endoscope manipulation, it is difficult to accurately and consistently position the sphincterotome for proper cannulation. The steerable sphincterotome of the present invention allows the physician to control the position of the distal tip of the device independently of the endoscope and adjust for inconsistencies in the device and the anatomy. According to the present invention, the handle to which the cutting wire is attached is freely rotatable relative to the catheter. The handle, secured to the cutting wire but rotatable relative to the shaft of the catheter, provides a mechanism to rotate the wire, transmitting the force to rotate the device tip. With the handle rotating independently of the shaft at the proximal end, the force can be applied directly to the distal tip without twisting the entire shaft. Also a rotation lock to maintain the orientation of the tip and/or a rotation marking, to indicate the amount of rotation may be included.

10 Claims, 17 Drawing Sheets

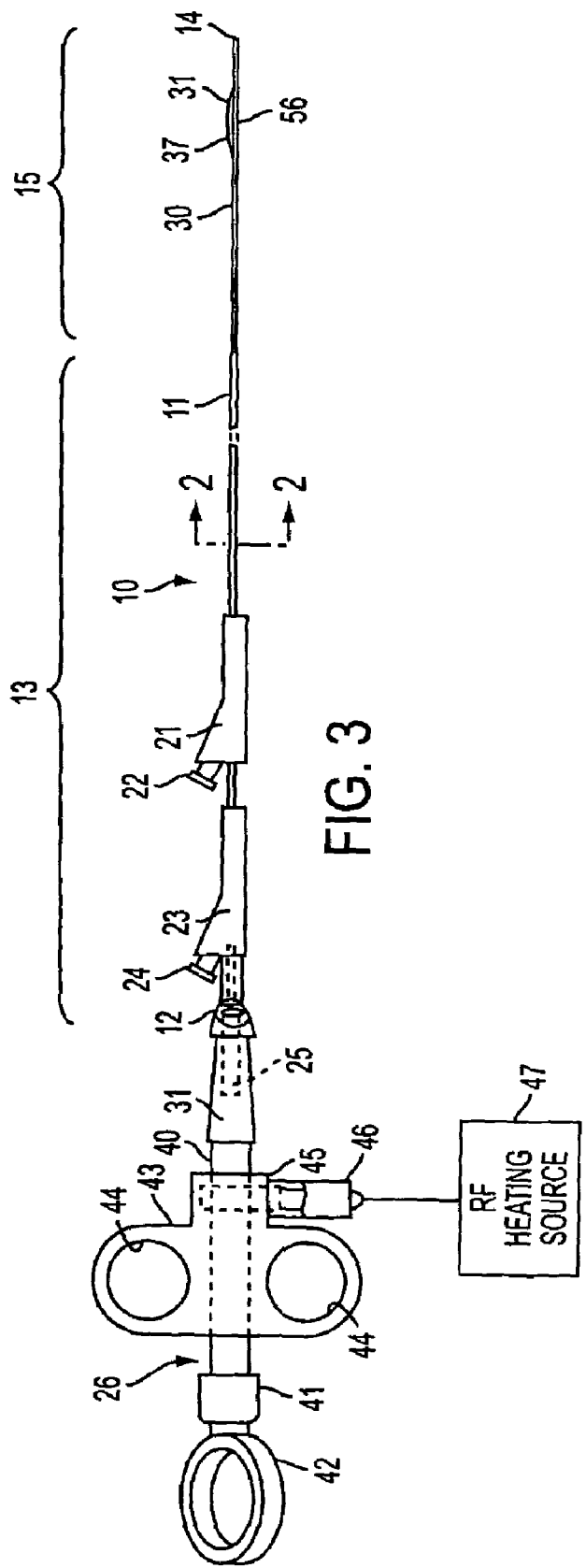
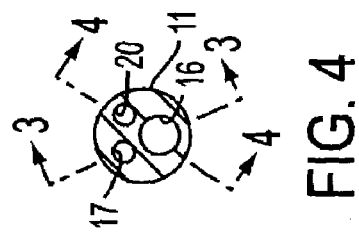

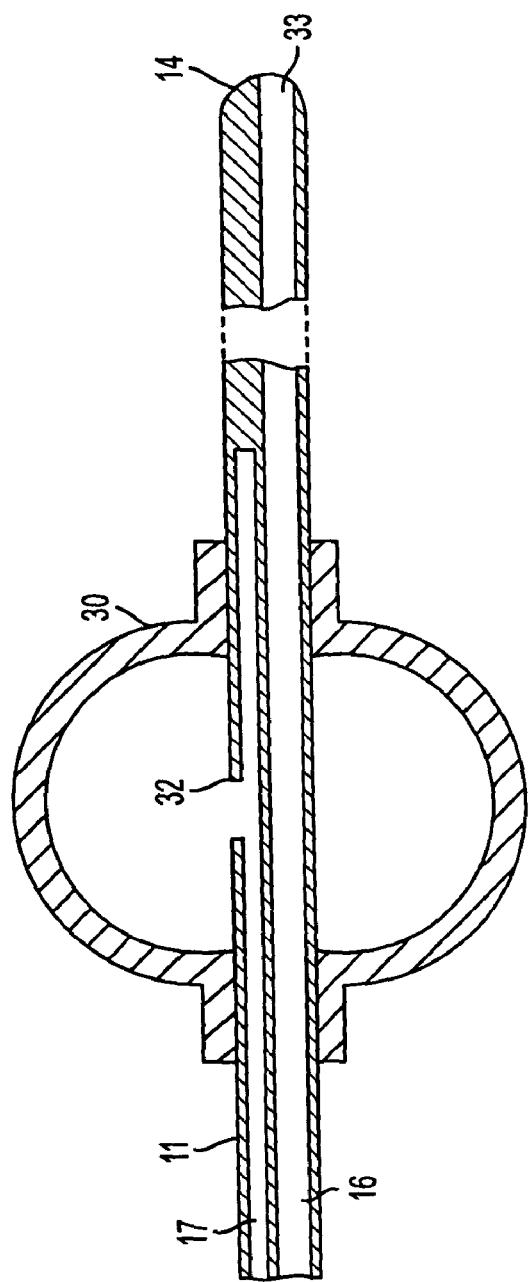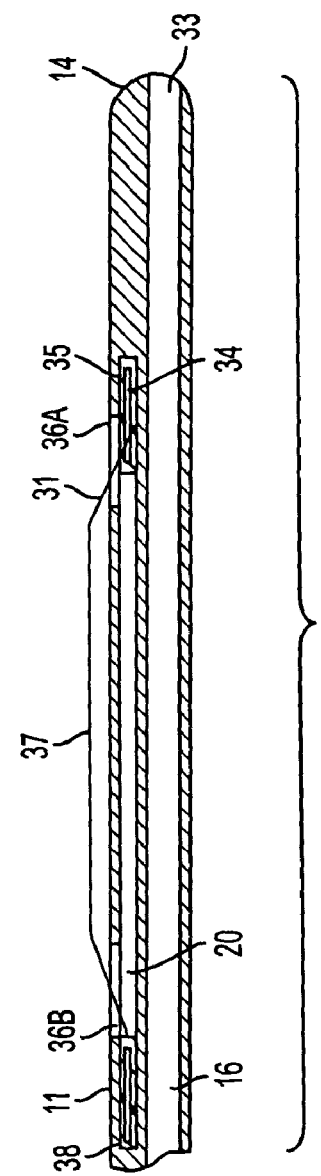

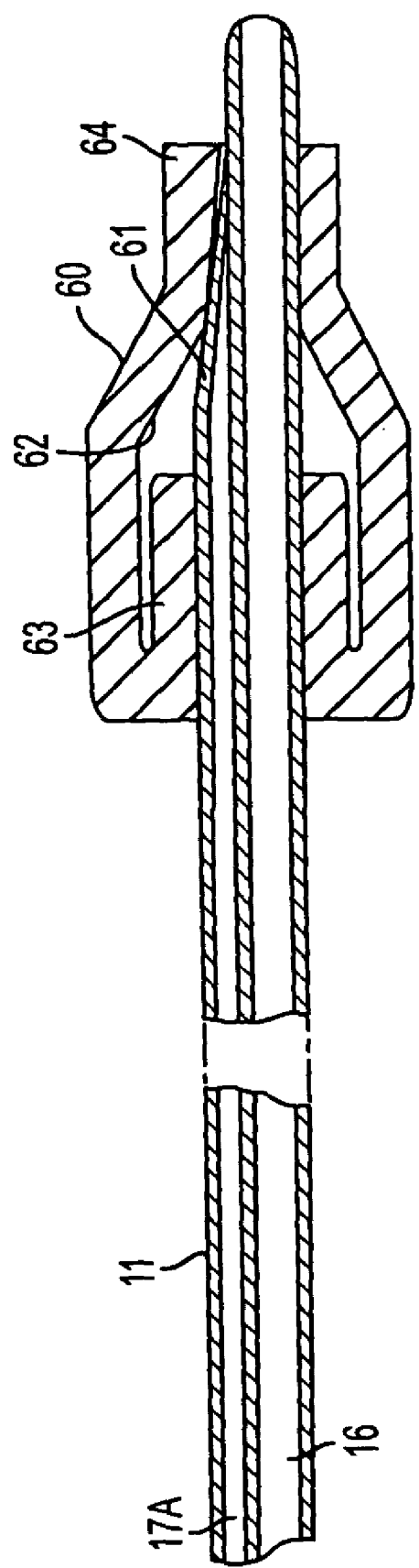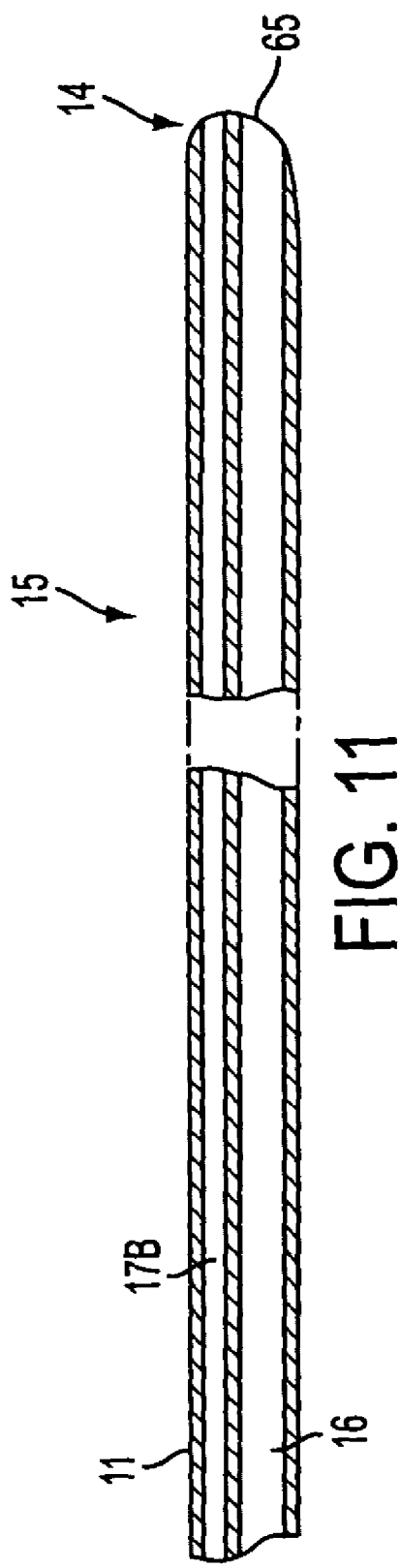

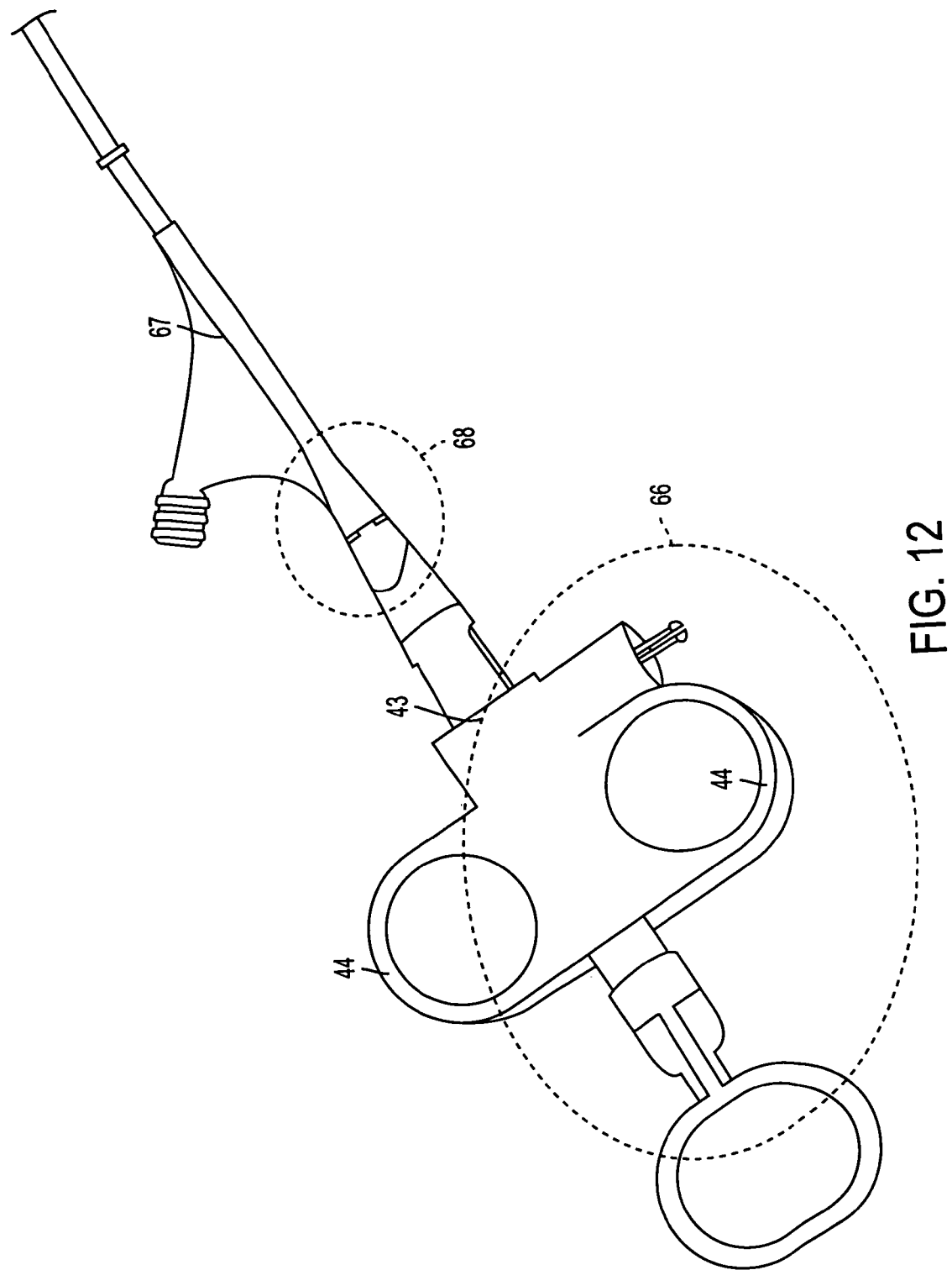

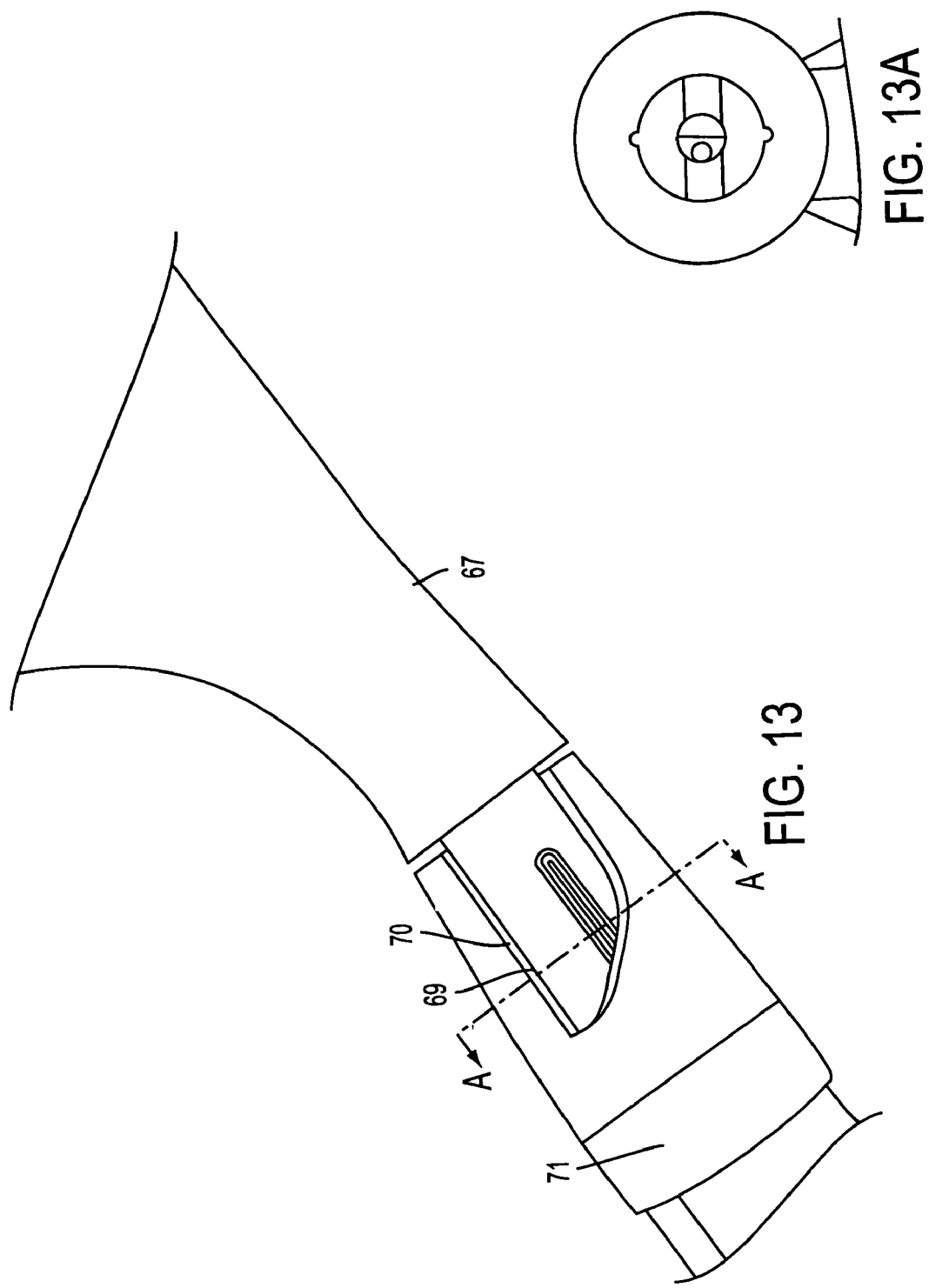

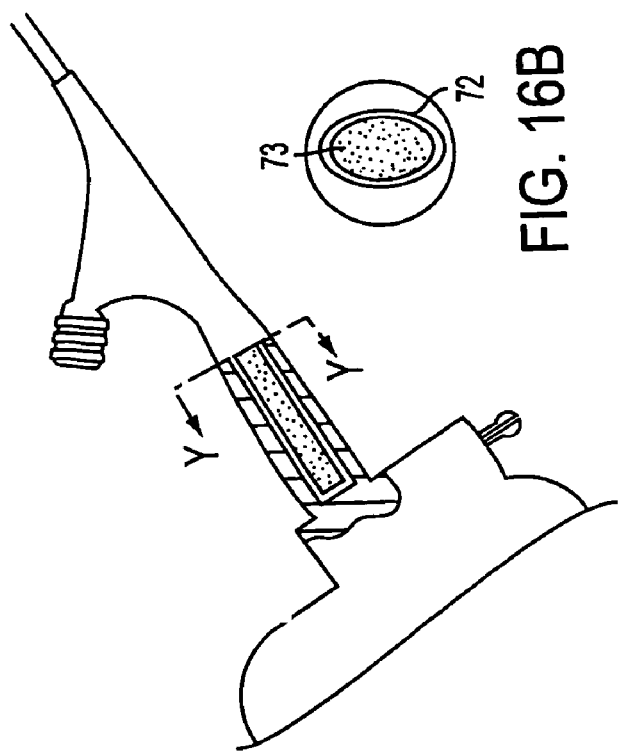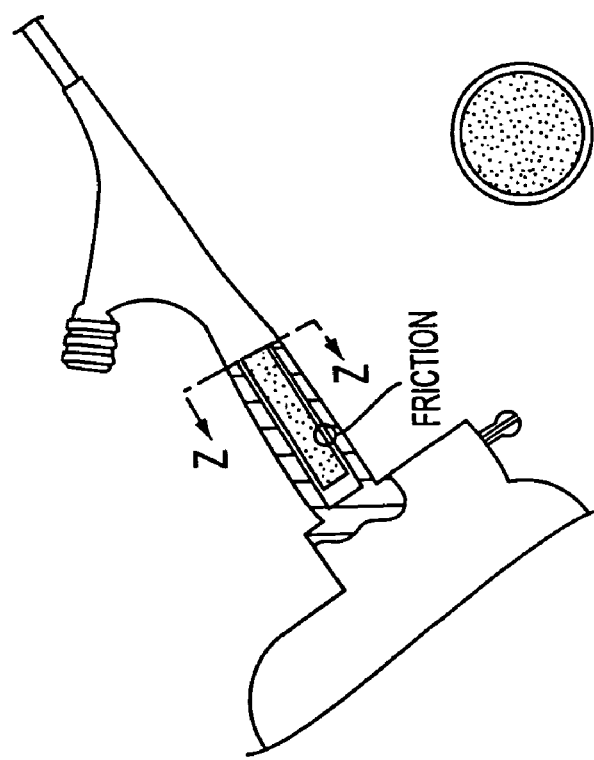

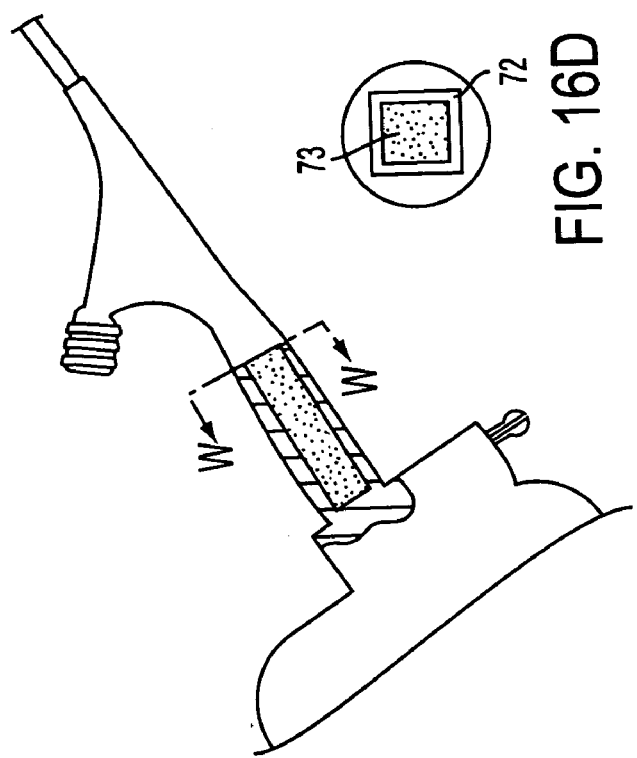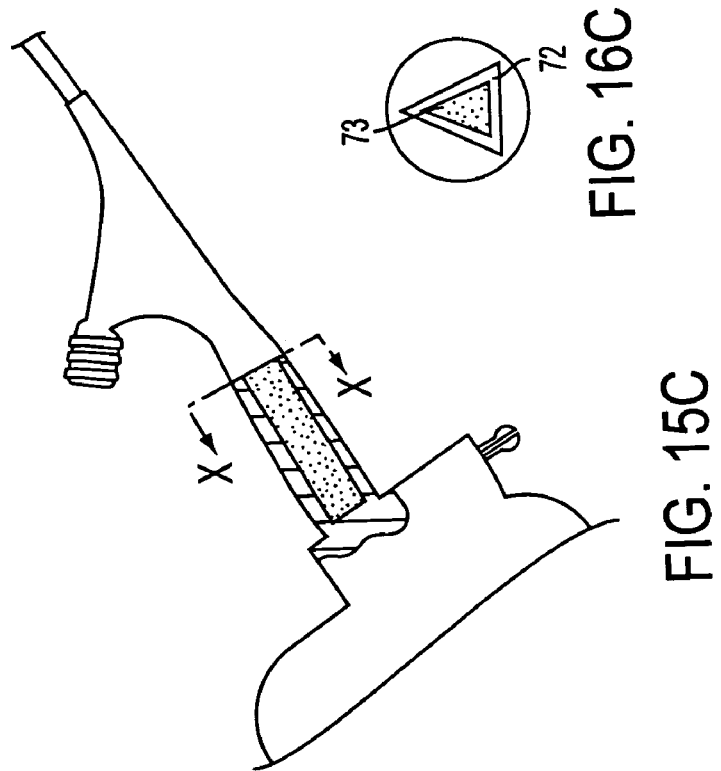

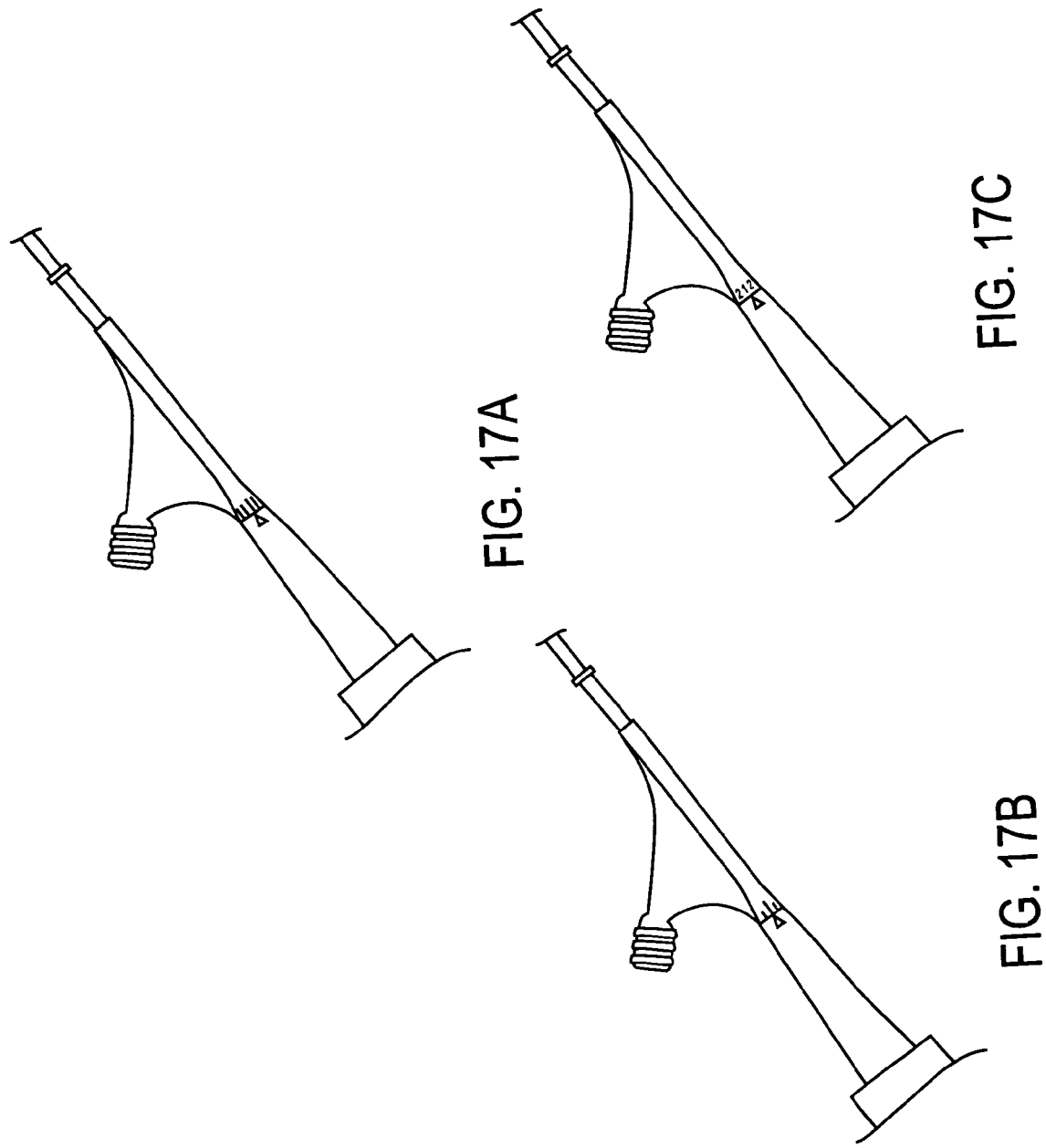

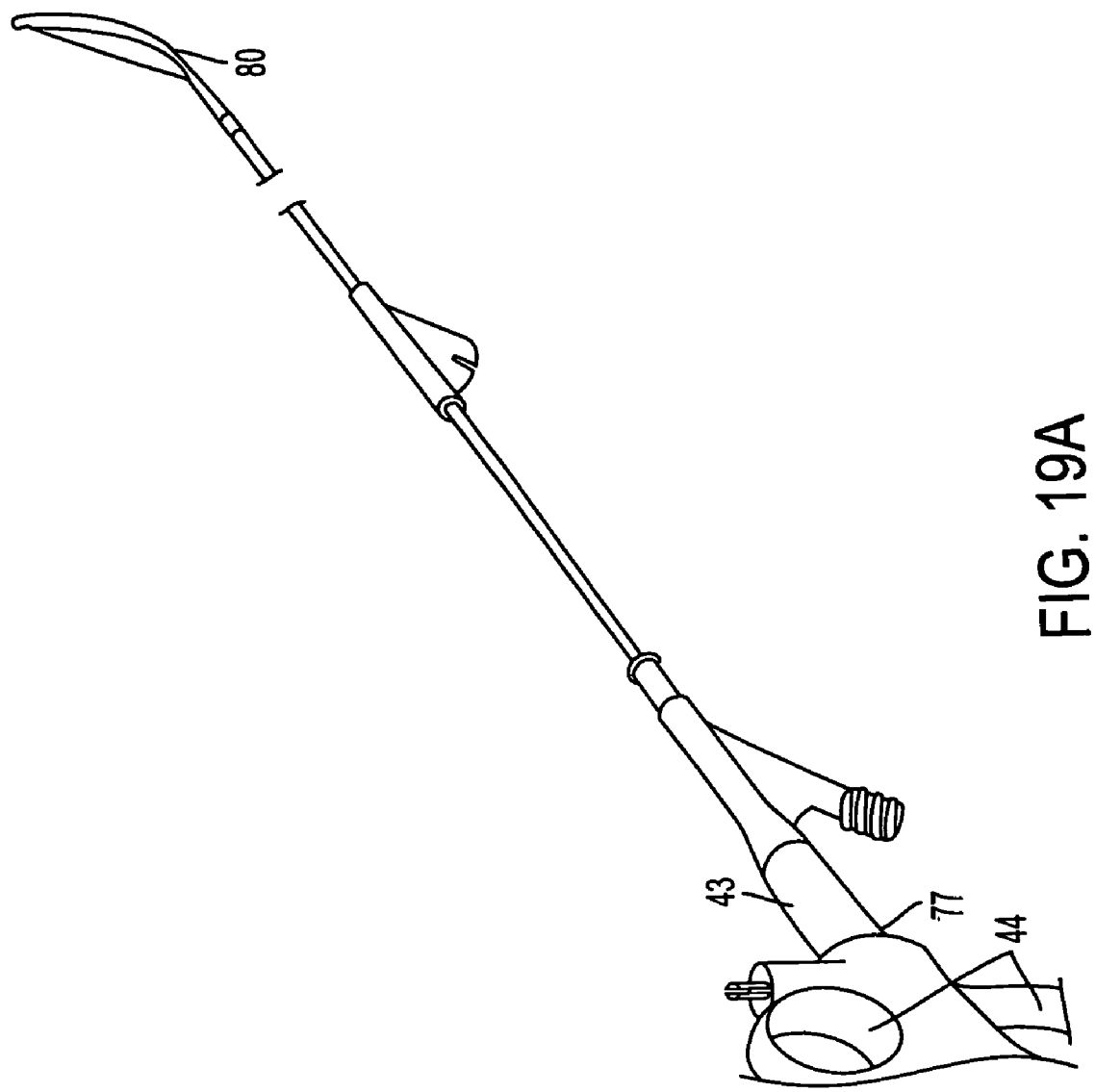

STEERABLE SPHINCTEROTOME AND METHODS FOR CANNULATION, PAPILLOTOMY AND SPHINCTEROTOMY

This application is a continuation of previously filed U.S. patent application Ser. No. 09/928,655, filed Aug. 14, 2001, entitled "STEERABLE SPHINCTEROTOME AND METHODS FOR CANNULATION, PAPILLOTOMY AND SPHINCTEROTOMY", issued Jan. 13, 2004, U.S. Pat. No. 6,676,659, which claims priority to U.S. Provisional Application No. 60/224,981 filed on Aug. 14, 2000.

BACKGROUND OF THE INVENTION

1. Field of the Invention

This invention generally relates to apparatus that is useful in performing diagnostic and therapeutic modalities in the biliary tree and more particularly to apparatus that is adapted for facilitating the diagnosis of gallstones in the bile duct and other portions of the biliary tree and the removal of such gallstones.

2. Description of Related Art

Historically the migration of gallstones into an individual's common bile duct was corrected by general surgical procedures. A surgeon would incise the bile duct and remove the gallstones and normally remove the gallbladder. In recent years less invasive treatment modalities have replaced these general surgical procedures and reduced patient trauma, long hospital stays and recovery periods.

For example, U.S. Pat. Nos. 4,696,668 and 4,781,677, both to Wilcox, disclose a treatment modality involving the administration of a dissolution agent in the bile duct to essentially dissolve any gallstones. More specifically, a catheter contains several lumens for inflating and deflating each of two balloons, venting bile, and infusing and aspirating the dissolution agent. Inflating the balloons occludes the bile duct at two spaced sites and creates a sealed spaced that receives the dissolution agent. As the space is sealed from the remaining biliary tree, the dissolution agent finds access to the gallbladder and any gallstones therein through the cystic duct with the exclusion of bile from the gallbladder fundus. The dissolution agent also will be confined in high concentration around bile duct gallstones. After the gallstones dissolve the balloons are deflated and the catheter can be withdrawn. In this particular approach, the catheter is directed into the biliary tree using a standard duodenoscope that passes through the alimentary tract. Although this and analogous approaches have the potential of minimizing patient trauma, such treatments require extended placement of the duodenoscope in the patient, exhibit low efficacy and introduce a potential for adverse reactions to the dissolution agents.

In an alternative approach, a surgeon directs a surgical extractor into the biliary tree through at least an incision in the bile duct. For example, in U.S. Pat. No. 3,108,593 to Glassman a surgeon incises both the bile duct and duodenum. Then the surgeon directs an extractor through the bile duct incision, biliary tree, sphincter of Oddi and duodenum to exit through the duodenum incision. This extractor includes a series of longitudinally spaced cages for trapping any gallstones in the bile duct and removing them through either of the incisions.

U.S. Pat. No. 4,627,837 to Gonzalo discloses a catheter device with a pair of inflatable balloons at its distal end. This catheter is led through an incision in the bile duct toward the duodenum. After the distal balloon passes through the sphincter of Oddi, both balloons are expanded to anchor the catheter in place. This enables the catheter to be used for irrigating and flushing through other lumens in order to capture any gallstone in the second balloon for removal through the incised bile duct.

In accordance with still another modality as for the treatment of strictures, a surgeon may insert a catheter device through the bile duct or duodenum for the purpose of dilating or enlarging the sphincter of Oddi. For example, U.S. Pat. No. 4,705,041 to Kim discloses a dilator that is directed through an incision in the bile duct and the sphincter of Oddi. An expandable tip dilates the sphincter of Oddi. U.S. Pat. No. 5,035,696 to Rydell discloses an electrosurgical instrument that is directed through the duodenum and to the sphincter of Oddi for performing a sphincterotomy. This apparatus contains a cutting wire that is heated to cut the sphincter muscle. U.S. Pat. No. 5,024,617 to Karpiel, discloses a similar device that can be directed through a duodenoscope. U.S. Pat. No. 5,152,772 to Sewell, Jr. discloses a device for performing a sphincterotomy that is directed through an incision in the bile duct and includes a knife for cutting the sphincter muscle.

The use of the duodenoscope and sphincterotomy devices, such as shown in the Rydell and Karpiel patents, enables an internist to diagnose and treat problems in the biliary tree with minimal patient invasion. For example, modalities as described in these patents eliminates the surgery needed for incising the bile duct. Consequently, these modalities can be performed as outpatient or day surgical procedures. These procedures greatly reduce patient trauma, the length of a hospital stay and recovery times. For example, if an internist determines that gallstones are present in the biliary tree, particularly the common bile duct, the internist can insert a duodenoscope into the duodenum to view the sphincter of Oddi. Then a first catheter can be advanced through the working channel of the duodenoscope with or without a guidewire and directed through the sphincter of Oddi into the biliary tree. Contrast agent injected through the catheter enables fluoroscopy or other imaging procedures to confirm the presence of gallstones within the biliary tree. Next the internist exchanges the first catheter for a second catheter for performing a sphincterotomy such as the types disclosed in the above-identified Rydell and Karpiel patents. The second catheter is then exchanged for a third catheter such as shown in the Glassman patent or some other equivalent retrieval catheter for drawings gallstones through the enlarged sphincter of Oddi. Thereafter the retrieval catheter is manipulated to release the gallstone into the duodenum. The catheter, any guidewire and the duodenoscope can then be removed to complete the procedure.

This procedure is significantly less traumatic to the patient than other prior art procedures because the only incision occurs during the sphincterotomy. However, this procedure as presently practiced requires three separate catheters and two catheter exchanges. These exchanges are required because the first, second and third catheters function solely to inject contrast agent to perform the sphincterotomy and to dislodge gallstones, respectively. The time required for performing each catheter exchange can increase patient trauma and increase the duration of the procedure and reduce efficiency. Moreover, each such procedure requires the use of two or three separate catheter devices.

SUMMARY

Therefore, an object of this invention is to provide apparatus for performing both diagnosis and additional therapeutic treatment without requiring a catheter exchange.

Yet another object of this invention is to provide apparatus that enables the removal of gallstones from the biliary tree by a procedure that reduces the number of required catheters and catheter exchanges.

Still another object of this invention is to provide a single catheter apparatus that can perform a sphincterotomy and remove gallstones in the common bile duct.

Yet another object of this invention is to provide a single catheter apparatus that can perform a sphincterotomy and inject contrast material into the biliary tree.

Still yet another object of this invention is to provide a single catheter apparatus that can inject contrast agent into the biliary tree, performing a sphincterotomy and remove gallstones in the bile duct into the duodenum.

Presently available products that may be modified according to the present invention include the Boston Scientific Ultratome, Ultratome XL, Stonetome, Flourotome, Tapertome, RX "C" Channel Sphincterotome, RX "U" Channel Sphincterotome, and RX Tapertome. Other products that may be modified according to the present invention include the Wilson Cook Canulatome, Wiltex Accuratome, Bard ProForma, and Olympus Clever Clevercut.

Accordingly, there is provided according to the present invention a method for cannulation of a common bile duct comprising threading a catheter through an appropriately placed endoscope, wherein said catheter comprises at least two and preferably three lumens, preferably a guide wire lumen, a contrast lumen, and a cutting wire lumen, whereby the handle of the device, secured to the cutting wire, may rotate independently of the catheter shaft and whereby the handle assembly is rotated to change the position of the distal tip independently of the scope position to achieve desired position for cannulation of the common bile duct. A rotation marking may be used to indicate the amount of rotation present and a rotation lock may be used to maintain the orientation of the tip.

The present invention also provides a method for sphincterotomy, whereby following cannulation, the handle of the mechanism may be rotated again, to the extent necessary to achieve the desired cutting position and cutting is effected by application of current to the cutting wire. Rotation lock and rotation markings may also be incorporated.

According to the invention, there is also provided a device comprising a catheter comprising two or preferably three lumens, preferably a guide wire lumen, a contrast fluid lumen, and a cutting wire lumen, whereby the catheter is rotatably attached to a handle fixed to the proximal end of the cutting wire. The proximal end of the catheter may terminate in a molded luer port assembly comprising entry points for the guide wire and for injection of contrast fluid. The guide wire and contrast lumens terminate at the distal end of the catheter. The handle and the catheter or molded luer port assembly may be designed to snap together to facilitate fast and inexpensive manufacture. Rotation lock and markings may also be included in this embodiment.

The present invention is an improvement of the devices and methods disclosed in U.S. Pat. Nos. 5,547,469, 5,868, 698 and U.S. Pat. No. 5,683,362 and in U.S. patent application Ser. No. 09/154,834 in the name of Rowland, et al., all owned by the owner of the present application, the common disclosure of which is incorporated herein and the subject matter of which is considered part of the present invention as set forth below. FIGS. 1 and 2 herein are original to the present application. Accordingly, original FIGS. 1-9 of the Rowland, et al. applications are renumbered herein as FIGS. 3 through 11.

In accordance with one aspect of this invention, apparatus can be used in a treatment modality including an enlargement procedure and another procedure to be performed. This apparatus includes a catheter with proximal and distal ends and proximal and distal portions. The catheter includes first, second and third generally parallel lumens. The first lumen has a greater diameter than either of the second and third lumens and the lumens each extend between proximal and distal portions of the catheter. The apparatus for performing the enlargement procedure extends through the second lumen for operating distally of the catheter in response to manipulations of an operator at the proximal end of the catheter. The first lumen has a proximal port for enabling access to the first lumen and the third lumen has a proximal port and a distal port for enabling the remote control of some other procedure.

In accordance with another aspect of this invention, apparatus is provided for removing objects from the biliary tree. This apparatus includes a catheter that is directed through the working channel of a duodenoscope and the sphincter of Oddi into the biliary tree. The catheter includes first, second and third lumens with the first lumen being larger than either the second or third lumens and the lumens generally extending between proximal and distal portions of the catheter along parallel axes. Apparatus for cutting the sphincter of Oddi includes a cutting wire extending through the second lumen and externally of the catheter means through a distal port along a length that is coextensive with part of the distal portion of the catheter. A handle attaches to the catheter at the proximal portion and to the proximal wire portion to control the position and orientation of the cutting wire. A rotation lock and marking may be incorporated to fix the orientation of the distal tip and to indicate the orientation of the distal tip respectively. An expansible balloon is mounted on the distal portion spaced from the cutting wire and can be inflated through the third lumen in order to move any gallstone in the biliary tree through the enlarged sphincter of Oddi.

In accordance with still another aspect of this invention, the apparatus is provided for directing contrast agent into the biliary tree and performing a sphincterotomy through the working channel of a duodenoscope. This apparatus includes a catheter that is directed through the working channel of the duodenoscope and the sphincter of Oddi into the biliary tree. The catheter includes first, second and third lumens with the first lumen being larger than either the second or third lumens and the lumens generally extending between proximal and distal portions of the catheter along parallel axes. Apparatus for cutting the sphincter of Oddi includes a cutting wire extending through the second lumen and externally of the catheter means through a distal port along a length that is coextensive with part of said distal portion of the catheter. A handle attaches to the catheter into the proximal wire portion to control the position and orientation of the cutting wire. A rotation lock and marking may be incorporated to fix the orientation of the distal tip and to indicate the orientation of the distal tip respectively. The proximal port of the third lumen connects to a contrast agent source and the third lumen delivers contrast agent into the biliary tree through a distal port in the distal end of the catheter.

BRIEF DESCRIPTION OF THE DRAWINGS

The various objects, advantages and novel features of this invention will be more fully apparent from a reading of the following detailed description in conjunction with the accompanying drawings in which like reference numerals refer to like parts, and in which:

FIG. 1a is a plan view of a snap in handle connection for the apparatus of FIG. 1;

FIG. 3 is a plan view of one embodiment of apparatus constructed in accordance with this invention;

FIG. 4 is a cross-section taken along lines 2-2 in FIG. 3;

FIG. 5 is a cross-section taken along lines 3-3 in FIG. 4;

FIG. 6 is a cross-section taken along lines 4-4 in FIG. 5;

FIG. 10 is a cross-section of an alternative embodiment of the apparatus as viewed generally along lines 3-3 in FIG. 4;

FIG. 11 is a cross-section of still another embodiment of this invention taken along lines 3-3 in FIG. 4;

FIG. 12 is a view of the rotatable handle of the present invention including a rotation lock;

FIG. 13 is a detailed view of the rotation lock of FIG. 12;

FIG. 13a is a sectional view along line A-A of FIG. 13;

FIGS. 15a-d show alternative embodiments of the rotation lock of the present invention;

FIGS. 16a-d show cross-sectional areas of the alternate embodiment of FIGS. 15a-d;

FIGS. 17a-c show three alternative embodiments of rotation markings for the present invention;

DESCRIPTION OF ILLUSTRATED EMBODIMENTS

Figure 1:
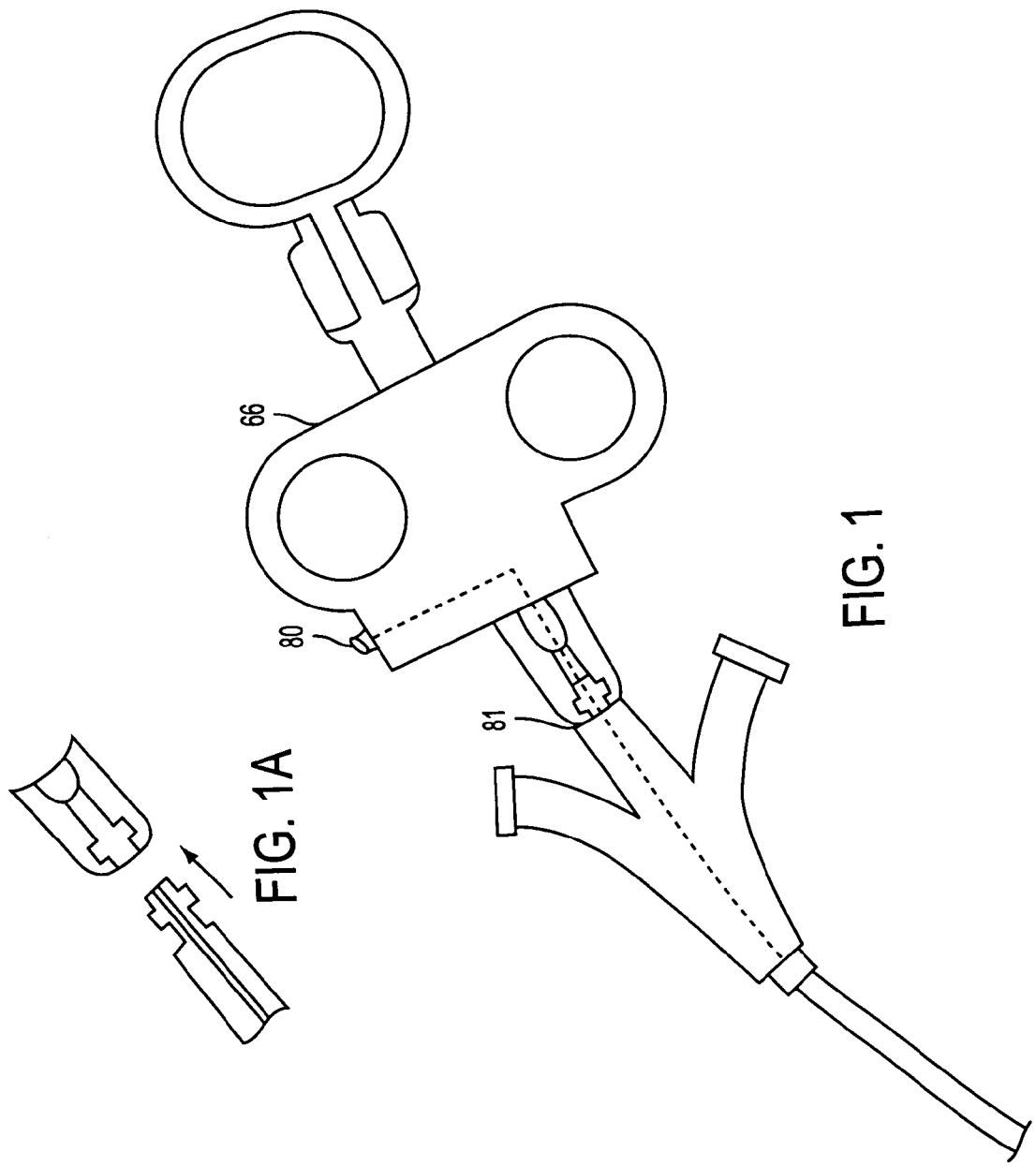
FIG. 1 is a plan view of one embodiment of apparatus constructed in accordance with the present invention with a rotatable handle attached to a cutting wire.

FIG. 3 depicts a catheter apparatus 10 that has the capability of injecting a contrast agent into the biliary tree, of performing a sphincterotomy and of dislodging a gallstone into the duodenum. The apparatus 10 includes a catheter 11 which, for purposes of definition, includes a proximal end portion 13 extending from a proximal end 12 and a distal end 14 with a distal portion 15 extending a short distance from the distal end 14. In a typical application, the catheter will have a working length of 200 cm and the distal end portion 15 will have a length of 6 cm to 9 cm. Normally the distal portion 15 will have a diameter that is smaller than the diameter of the proximal portion to increase the flexibility of the distal portion 15. The reduction in diameter also makes the tip less traumatic and allows the tip portion to reach smaller passages while allowing the larger proximal portion to provide necessary hoop strength and rigidity, particularly where the proximal portion 13 is coextensive with the working channel of a duodenoscope. For example, the proximal and distal portions might have diameters corresponding to 7 Fr and 5.5 Fr catheter sizes (i.e., 0.09" and 0.07" respectively).

As shown particularly in FIG. 4, the catheter 11 has three lumens. A first lumen 16 has a diameter that is greater than either a second lumen 17 or a third lumen 20. In one particular embodiment the lumen 16 has a diameter of 0.040" in the proximal portion 13 that reduces to about 0.037" in the distal portion 15 to receive a standard 0.035" guidewire. In addition the lumen 16 is offset from the center of the catheter 11.

The lumens 17 and 20 are each smaller in diameter than the lumen 16 and are radially offset from the centerline of the catheter, from each other and from the lumen 16. In one particular embodiment the lumens 17 and 20 each have internal diameters of 0.028" in the proximal portions 13 that reduces to about 0.020" in the distal portion 15. As described later, this lumen 20 carries a cutting wire for performing a sphincterotomy and for allowing the infusion of a contrast agent at reasonable rates. The angular spacing between the lumens 17 and 20 is about 45 degrees and the angular spacing between the first lumen 16 and each of the lumens 17 and 20 each is about 157.5 degrees. In this configuration and with these dimensions the proximal portion 13 readily passes through the working channel of any duodenoscope.

Referring again to FIGS. 3 and 4, each of the lumens 16, 17 and 20 includes an entry port in the proximal portion 13 and an exit port in the distal portion 15. Generally, and as described in more detail later, the first lumen 16 has an exit port through the distal end 14 while the exit ports for the lumens 17 and 20 can be sited at different locations in the distal portion 15 depending upon a particular application.

In FIG. 3, the entry ports in proximal portion 13 adjacent the proximal end 12 include an entry port 21 that provides access to the lumen 16 and includes an optional Leur lock fitting 22. A proximally positioned entry port 23 provides access to the lumen 17 and includes an optional Leur lock fitting 24. A proximal entry port 25 for the lumen 20 is located coextensively with a portion of a handle 26 attached to the proximal end 12.

Referring to the distal end portion 15, the catheter 11 in this particular embodiment carries an expansible balloon 30 proximally of the excursion of a cutting wire 31 externally of the catheter 11. As shown in FIG. 5, the lumen 17 emerges at a distal exit port 32 through the side of the catheter 11 with the interior of the expansible balloon 30. An extension of the lumen 17 beyond the distal port 32 is sealed by known, methods of manufacture. Consequently, fluid forced through the entrance port 23, as by a syringe (not shown) attached to the Leur lock fitting 24, expands the balloon 30 into an occluding orientation as shown in FIG. 5 with an inflated diameter in the range up to 20 mm.

As will also be apparent from viewing FIGS. 5 and 6, the first lumen 16 extends through the catheter 11 and terminates with an exit port 33 in the distal end 14. Thus the lumen 16 is adapted for receiving a guidewire through the entrance port 21 that will extend through the catheter 11 and exit the distal end 14 and allow the catheter to slide over that guidewire.

Referring to FIG. 6, a distal end 34 of the cutting wire 31 attaches to a clamp 35 formed at the distal end of the lumen 20. Spaced skived ports 36A and 36B allow an active portion 37 of the cutting wire 31 to emerge from the catheter 11 through the skived aperture 36A, parallel the catheter 11 exteriorly thereof and return into the lumen 20 through the port 36B and a reinforcing sleeve 38. The cutting wire 31 then extends through the lumen 20 to the handle 26 shown in FIG. 1 where it emerges as a proximal end portion 40.

The handle 26, as shown in FIG. 3, includes a central member 41 terminating with a thumb ring 42. The central member 41 extends through and slides with respect to a body section 43 having opposed finger rings 44. The central member 41 also attaches to the catheter 11, and is therefore an extension of the catheter 11. The member 43 additionally includes an internal connector 45 for clamping the proximal end 40 of the cutting wire 31. Thus, when the body 43 is at its distal position as shown in FIG. 3, the distal portion of the catheter 15 is in essentially straight line as shown in FIG. 3 with the active portion 37 of the cutting wire 31 being closely adjacent the catheter 11. Retracting the body portion 43, causes the cutting wire 31 to bend the distal end upwardly as shown in FIG. 3 to a position that is essentially at right angles to the main axis of the catheter, as will be shown later.

The connector block 45 and the cutting wire 31 are generally conductive members that attach through an RF connector 46 to an RF heating source 47. The use of such RF heating sources 47 for energizing a cutting wire 31 thereby to cut the sphincter muscle is well known in the art and represents one possible sphincterotomy procedure that can be adapted for the apparatus of this invention and is not described further.

Figure 7:
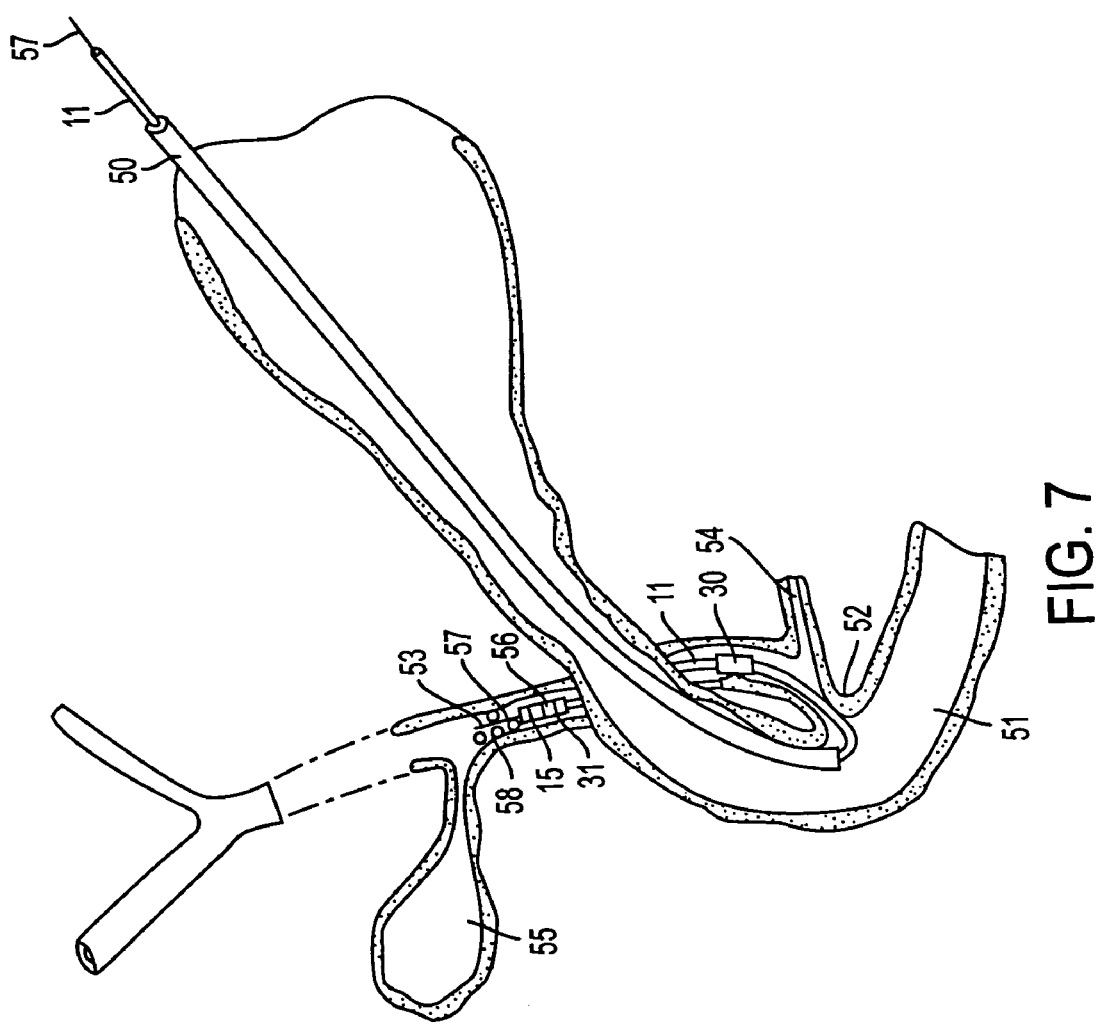
FIG. 7 depicts the apparatus of FIG. 3 positioned through a duodenoscope for injecting contrast agent into the biliary tree.

With this description of the apparatus structure, it will now be possible to understand its use in a particular application. FIG. 7 discloses, in a partially broken and schematic view, the positioning of a duodenoscope 50 in the duodenum 51 adjacent the sphincter of Oddi 52. A catheter 11 such as constructed in FIG. 3 passes through the sphincter of Oddi 52 into the common bile duct 53, bypassing the pancreatic duct 54. The distal end 14 does not extend to the gallbladder 55.

Fluoroscopy allows the appropriate positioning by utilizing a series of radio-opaque markers 56 at the distal portion 15 that may include the clamp 35 and the reinforcing sleeve 38 in FIG. 6. The catheter 11 can be positioned with or without the presence of a guidewire 57 in the lumen 16 shown in FIGS. 4, 5 and 6. For purposes of injecting the contrast agent, any guidewire 57 can be withdrawn to allow the contrast agent to be injected through the lumen 16 for purposes of fluoroscopic examination to confirm the presence of one or more gallstones 58. It is also possible during the operation to expand the balloon 30 to occlude the bile duct 53 and block any migration of contrast agent into the duodenum 51 or the pancreatic duct 54.

Figure 8:
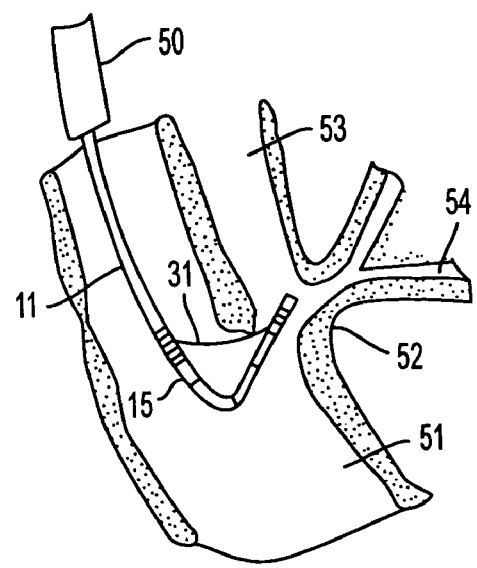
FIG. 8 is an enlarged view that depicts the orientation of the apparatus in FIG. 3 for performing a sphincterotomy.

FIG. 8 is an enlarged view showing the duodenum 51, sphincter of Oddi 52, portions of the pancreatic duct 54 and the common bile duct 53. In FIG. 8 the catheter 11 has been positioned relative to the duodenoscope 50 through the opening of the sphincter of Oddi 52. The handle 43 in FIG. 3 has been drawn proximally to deflect the distal portion 15 into essentially a right angle configuration such that the cutting wire 31 abuts a portion of the sphincter of Oddi 52. The application of RF heating to the cutting wire 31 then will cut the sphincter of Oddi 52 and enlarge the opening therethrough. As will be apparent, the sphincterotomy is performed with direct visualization of the sphincter of Oddi through the duodenoscope.

Moreover, as has been observed by others, catheters having guidewire and cutting wire lumens tend to assume a particular angular orientation when the distal portion 15 emerges from the duodenoscope. This orientation is essentially independent of, the angular position of the catheter when it is inserted into the duodenoscope. The offset nature of the lumen 20 as shown in FIG. 4, improves the location of the cutting wire 31 as the distal portion 15 passes through the sphincter of Oddi 52. Specifically the angularly offset brings the cutting wire 31 into better alignment with the common bile duct 53 and displaces the cutting wire from the pancreatic duct 54.

Figure 9:
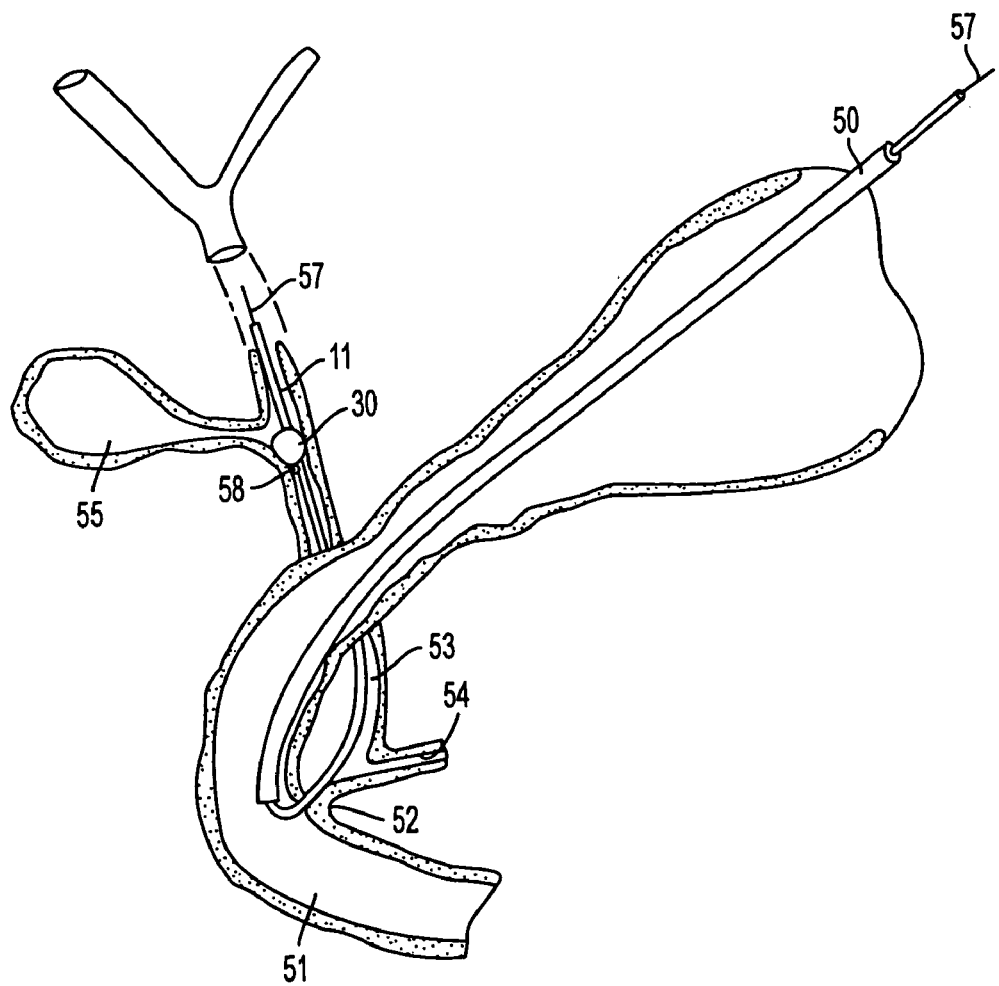
FIG. 9 depicts the apparatus of FIG. 3 positioned through a duodenoscope for dislodging material within the common bile duct.

FIG. 9 depicts the catheter after the sphincterotomy and after the catheter 11 is advanced over the guidewire 57, if used. FIG. 9 also discloses the catheter 11 after the balloon 30 has been moved beyond a gallstone 58 in the bile duct 53. The balloon 30 is expanded so that upon withdrawal of the catheter 11 the balloon 30 will dislodge the gallstones 58 and sweep them through the sphincter of Oddi 52 into the duodenum 51.

As will now be apparent from the description of the particular catheter apparatus 10 shown in FIG. 3 and its use as discussed with respect to FIGS. 7, 8, and 9, the single catheter apparatus of this invention is capable of providing diagnostic contrast agent injection, of performing a sphincterotomy and of dislodging gallstones in the common bile duct or other portions of the biliary tree without having to exchange a catheter. Moreover, positioning and sizing of the lumens enables these functions to be performed with a catheter apparatus that is readily adapted for use in the working channels of standard duodenoscopes. Consequently the gallstones can be removed from the biliary tree without bile duct incisions and accompanying surgical procedures, as duodenoscope can be introduced through the alimentary tract. Consequently the entire procedure is adapted for being performed more rapidly than prior art procedures and with fewer components. The net effect is to reduce patient trauma and the overall time and cost of conducting the procedure.

In FIG. 3 the balloon 30 is located proximally of the cutting wire 31. FIG. 10 discloses an alternative embodiment in which a balloon 60 is located distally of the cutting wire 31. More specifically, the distal end of a lumen 17A, corresponding to the lumen 17 in FIGS. 5 and 6, is sealed. A side facing exit port 61 skived or otherwise formed in the catheter 11, opens into a chamber 62 formed by the balloon 60. A first sealing portion 63 and a sealing portion 64 of the balloon 60 connect proximally and distally of the aperture 61 respectively and seal the chamber 62.

Introduction of a balloon inflation fluid through the lumen 17A expands the balloon 60 into an occluding orientation corresponding to the orientation of the balloon 30 shown in FIG. 5. Retraction of the catheter 11 with the distal balloon 60 inflated enables withdrawal of a gallstone from the bile duct. This particular embodiment is particularly adapted when it is determined that a gallstone is located high in the biliary tree to minimize the incursion of the distal portion 15 through the biliary tree beyond the gallstone or in any application in which the internist desires to minimize the length of the distal portion 15 that extends beyond the occluding balloon.

FIG. 11 discloses another embodiment of this invention for enlarging the sphincter of Oddi and performing another procedure, such as injecting a contrast agent into the biliary tree, as might be used in the diagnosis and treatment of a stricture in the biliary tree. In this particular embodiment an exit port 65 from the lumen 17B is located in the distal end 14 of the distal portion 15. The lumen 16 then can be used for a guidewire and the lumen 17B, for injecting the contrast agent directly into the biliary tree while the guidewire remains in place. The apparatus would then be positioned to perform a sphincterotomy without having to exchange a catheter should the procedure be warranted.

As still another alternative, the internist could utilize a conventional catheter for purposes of injecting the contrast agent to determine the need for gallstone removal. If treatment were indicated, the internist could then utilize apparatus as shown in FIG. 3 with a single exchange over the guidewire that would pass through the lumen 16 as previously described.

Therefore, it will now be apparent that apparatus constructed in accordance with this invention attains the several objects and the advantages of this invention. More particularly, catheter apparatus constructed in accordance with this invention allows the injection of a contrast agent, the performance of a sphincterotomy and dislodging gallstones from the common bile duct through the enlarged sphincter of Oddi into the duodenum all without requiring any catheter exchanges. Moreover, this apparatus allows such a procedure to occur through a duodenoscope to minimize patient trauma. The use of a single catheter with an elimination of catheter exchanges further reduces the time and costs associated with the use of multiple, single-function catheter devices.

As will be apparent from the foregoing description, many alterations can be made to the specifically disclosed embodiments. Different balloon structures can be used and located at alternative positions. Different cutting wire embodiments and orientations can be used. Thus, although this invention has been disclosed in terms of certain embodiments, it will be apparent that many modifications can be made to the disclosed apparatus without departing from the invention. In particular, it is considered that all of the foregoing embodiments may be used in conjunction with a handle fixed to the cutting wire but rotatable relative to the catheter. A rotation lock fixing the orientation of the cutting wire and/or a rotation marking, indicating the amount of rotation may be included with the current invention. Therefore, it is the intent of the appended claims to cover all such variations and modifications as come within the true spirit and scope of this invention.

Consistent therewith, the following subject matter claimed in the Rowland, et al patents and applications is specifically claimed in connection with the subject matter specific to the present application, namely, a handle fixed to the cutting wire and rotatable relative to the shaft of the catheter, whereby turning of the handle independently of the catheter and independently of the endoscope causes the distal tip of the device to rotate independently of the endoscope allowing the surgical team greater control over the position of the device for cannulation and subsequently for sphincterotomy A rotation lock fixing the orientation of the cutting wire and/or a rotation marking, indicating the amount of rotation may be included with the current invention.

Figure 2:
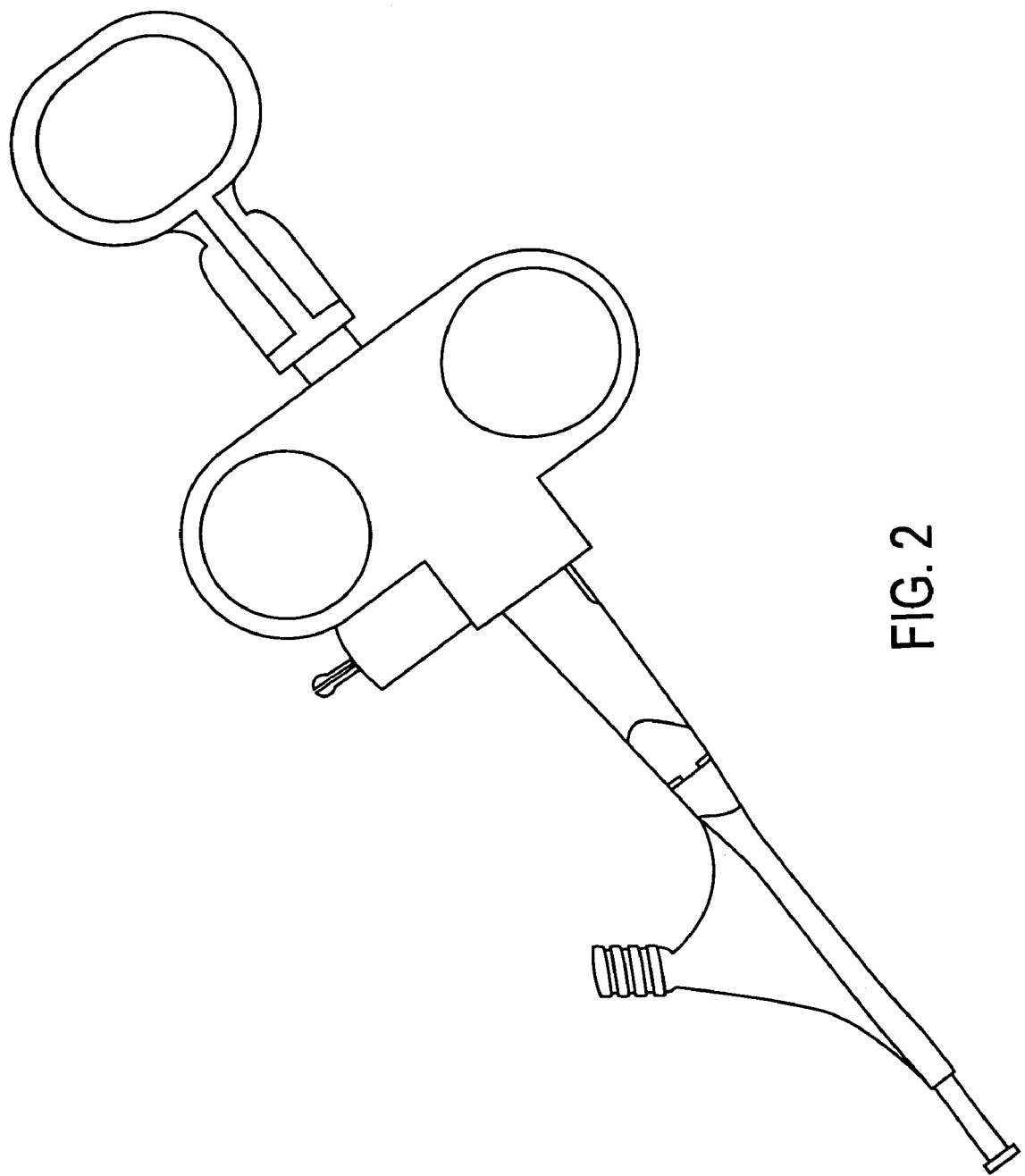
FIG. 2 is a view of an alternative embodiment of the rotatable handle of the present invention.

Due to inconsistencies in the sphincterotome, anatomy, and endoscope manipulation, it is difficult to accurately and consistently position the sphincterotome for proper cannulation. The steerable sphincterotome of the present invention allows the physician to control the position of the distal tip of the device independently of the endoscope and adjust for inconsistencies in the device and the anatomy. According to the present invention, the handle to which the cutting wire is attached is freely rotatable relative to the catheter. Rotating the handle of the present invention induces a twisting of the attached cutting wire which allows orientation of the distal end without rotating the proximal end of the attached catheter. See FIGS. 1 and 2. Handle 66, secured to the cutting wire at 80 but rotatable relative to the shaft of the catheter at 81, provides a mechanism to rotate the wire, transmitting the force to rotate the device tip. With the handle rotating independently of the shaft at the proximal end, the force can be applied directly to the distal tip without twisting the entire shaft. Also a rotation lock to maintain the orientation of the tip and/or a rotation marking, to indicate the amount of rotation may be included. An integrated molded luer port assembly for 2 and 3 lumen catheters may be provided to snap into the rotatable handle, to facilitate fast and economical manufacturing, as shown in FIGS. 1 and 1a. Alternatively, prior art serial lumen ports may be configured to snap into the rotatable handle as shown in FIG. 2.

Referring to FIG. 12, the present invention also contains a feature known as a rotation lock. Rotation lock 68 allows the user to maintain the orientation of the tip at all times. This is done by maintaining the position of handle 66 relative to bifurcation connector 67 after the handle has been rotated. Rotation lock 68 allows the user to release handle 66 at any time during the procedure, while maintaining the orientation of handle 66 and preventing further rotation while the lock is engaged. Maintaining the position of handle 66 maintains the orientation of the distal tip in the desired orientation. Maintaining the orientation of the distal tip reduces the amount of time and effort required to cannulate if the distal tip moved. Preventing undesired movement of the distal tip may also prevent patient injury.

Referring to FIG. 13, two pair of mating detents 69 and slots 70 may be used to create this rotation lock. Detents 69 and slots 70 are located along the central axis of body 71, at the intersection of body 71 and bifurcation connector 67. In FIG. 13, the two pair of detents 69 and slots 70 are located 180° apart, relative to the central axis. This creates a lock position every half rotation of handle 66. During use of the device, as handle 66 is rotated, detents 69 become disengaged from slots 70. As detents 69 become disengaged, they compress slightly. As handle 66 reaches a position 180° from where rotation began, detents 69 recover from their compressed state, and engage with slots 70 once again. As detents 69 traverse from one position to the next, there is a noticeable amount of friction between the mating components. This friction is great enough that handle 66 can be released at any time without fear of losing the orientation position of the distal tip.

Rotation lock 68 also serves a secondary function of keeping the distal tip locked in the home position while the catheter is being removed from the package, inserted into the endoscope, and manipulated through the endoscope. Without this feature, the initial orientation position of the distal tip would become unpredictable. FIG. 13a shows a detailed diagram of the interaction between detents 69 and slots 70.

Figure 14:
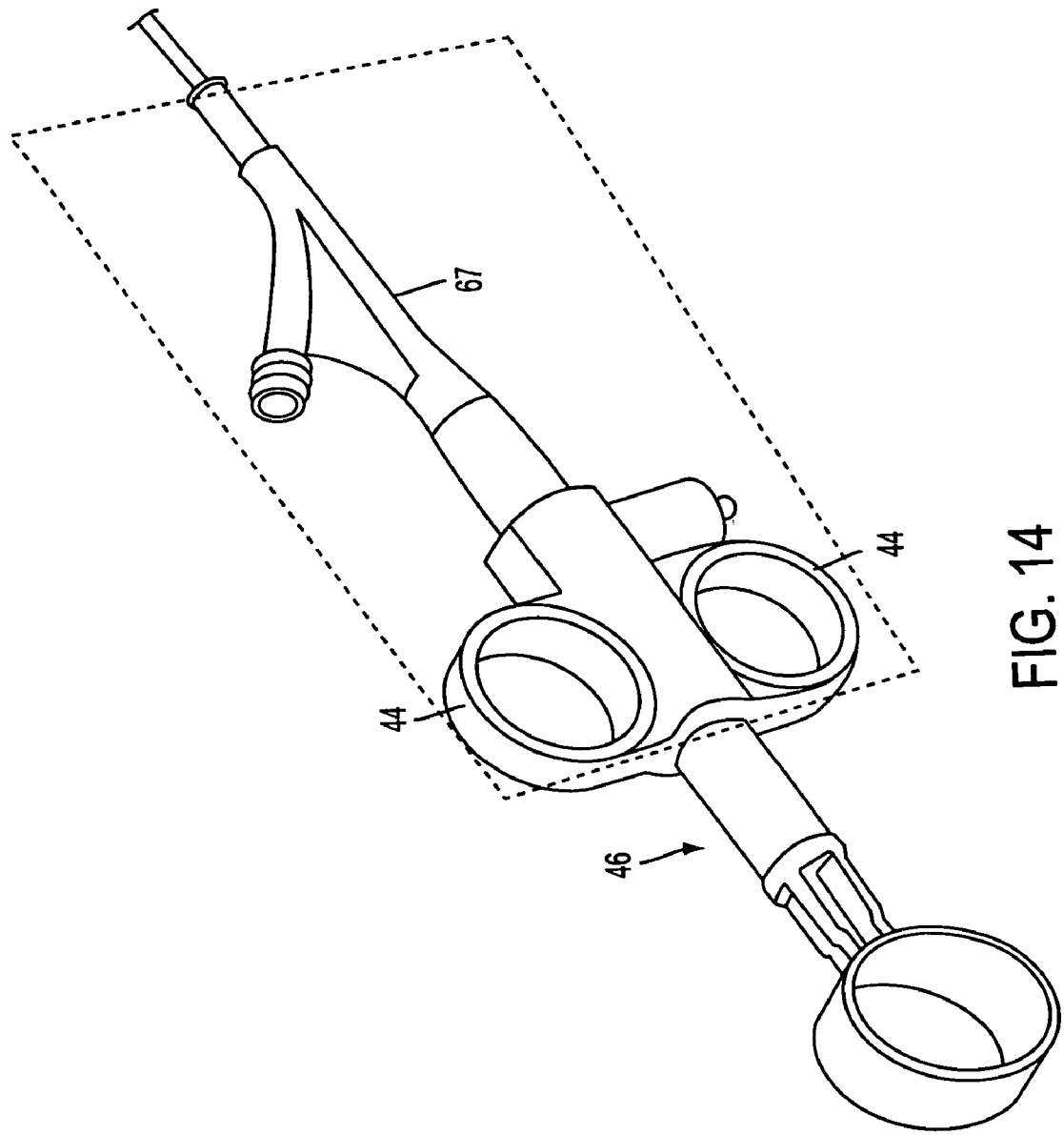
FIG. 14 shows an alignment between the rotatable handle and the bifurcation connector showing zero rotation of the rotatable handle.

Referring to FIG. 14, when detents 69 and slots 70 are engaged, bifurcation connector 67 and finger rings 44 all lie in the same plane. This acts as the rotation marker. Whenever finder rings 44 are rotated into the same plane as bifurcation connector 67, the rotation lock is engaged, thus signaling 180° of rotation from the last position. The use of a marker such as this allows the user to more easily keep track of how much handle 66 has been rotated. This is helpful if the user desires to move the distal tip back to its original position. In effect, the user will know, for example, that handle 66 has been rotated three clicks from the original position. Therefore, to return handle 66 to the original position, it must be rotated three clicks in the opposite direction.

FIGS. 15a-15d show alternative embodiments of rotation lock 68. FIG. 15a shows a pure frictional lock. The connection of bifurcation connector 69 to the handle 66 could be designed such that rotation lock 68 is purely a function of frictional interference between the two components. Alternative embodiments could include different types of assembly joints to create this friction. In the primary embodiment, the assembly of the two components is accomplished by mating a male post of the bifurcation connector to a female hole of the same size and shape. Alternative embodiments could reverse this, so that the male protrusion is part of the main body of handle 66. The friction lock could also be built into the mating faces of main body and bifurcation connector, which are perpendicular to the major axis. FIG. 16a shows a cross section of the rotation lock along Z-Z of FIG. 15a.

FIG. 15b shows a oval post lock embodiment of the present invention. The connection of bifurcation connector 67 to handle 66 could also be designed incorporating an ovalized male post 73 and female hole 72. In this embodiment, as, handle 66 is rotated relative to bifurcation connector 67, ovalized hole 72 would deform, allowing oval post 73 to rotate. As handle 66 reached a rotation of 180°, ovalized hole 72 would conform back to its original shape, thus locking handle 66 in place. As shown in FIGS. 15c and 15d, this basic concept may be expanded to incorporate other shapes rather than oval as shown in FIG. 15b. One of ordinary skill in the art would appreciate that the shape of the geometry however, governs the degrees of rotation between locked positions. For example, if post 73 and ovalized hole 72 configuration were made up of mating equilateral triangles (FIG. 15c), there would be 120° of rotation between locked positions. Using a square configuration (FIG. 15d), would give 90° between locked positions. FIG. 16b, illustrates the cross-sectional area across Y-Y of FIG. 15b. FIG. 16c illustrates the cross-sectional area of FIG. 15c across X-X and FIG. 16d illustrates the cross-sectional area of FIG. 15d along cross-section W-W.

FIGS. 17a-c show alternative embodiments by which a rotation marker may be created and included in the present invention. One of ordinary skill in the art would understand these embodiments may be expanded. To aid the user in knowing exactly how much handle 66 has been rotated from its original and/or last position, several forms of visual markers can be incorporated into the design. One alternative embodiment is comprised of a set of lines placed radially, around the major axis, at the area where the main body and bifurcation connector 67 meets (FIG. 17a). A single line on the stationary component, bifurcation connector 67, would match up with a corresponding line on body 43. As handle 66 is rotated relative to bifurcation connector 67, the series of lines on the body would rotate past the stationary line on bifurcation 67. Each line would indicate an incremental amount of movement. For example, if there were four, equally spaced lines on the body, each line that passed the marker on the bifurcation connection would signify 90° of rotation.

This feature could be further enhanced by many methods. A series of numbers rather than lines could be used to signify the amount of rotation (FIG. 17b). Alternating colors could also be used to signify the amount of rotation. Alternating line patterns could be used as well (FIG. 17c).

Another alternative embodiment may use audible tones to make the user aware of the amount of rotation. One method for doing this would be able to design the rotation lock features so that a click is clearly audible at predetermined points along the rotational travel of the body.

Figure 18A:
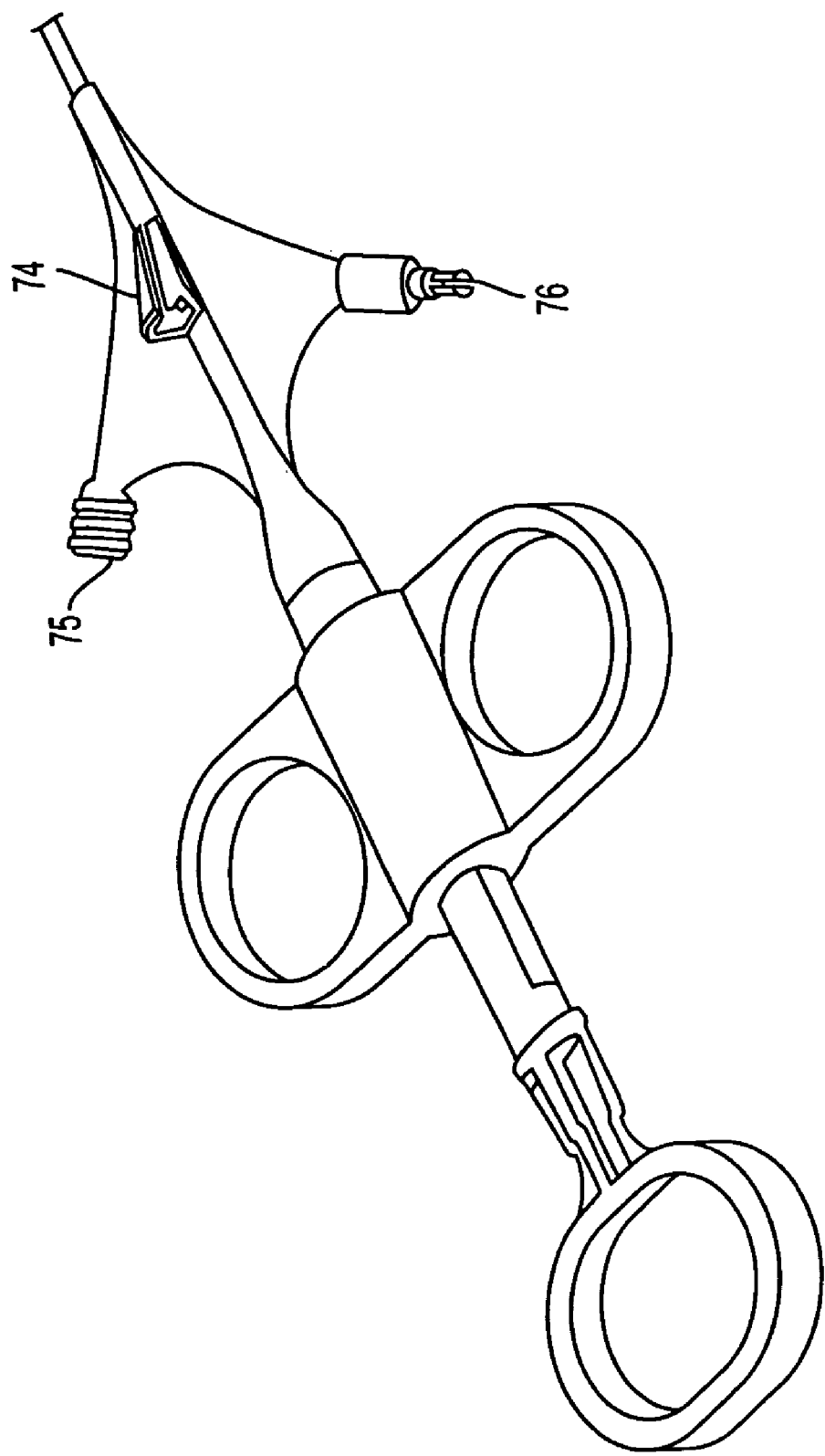
FIGS. 18a & b illustrate alternatives of bifurcation connectors.
Figure 18B:
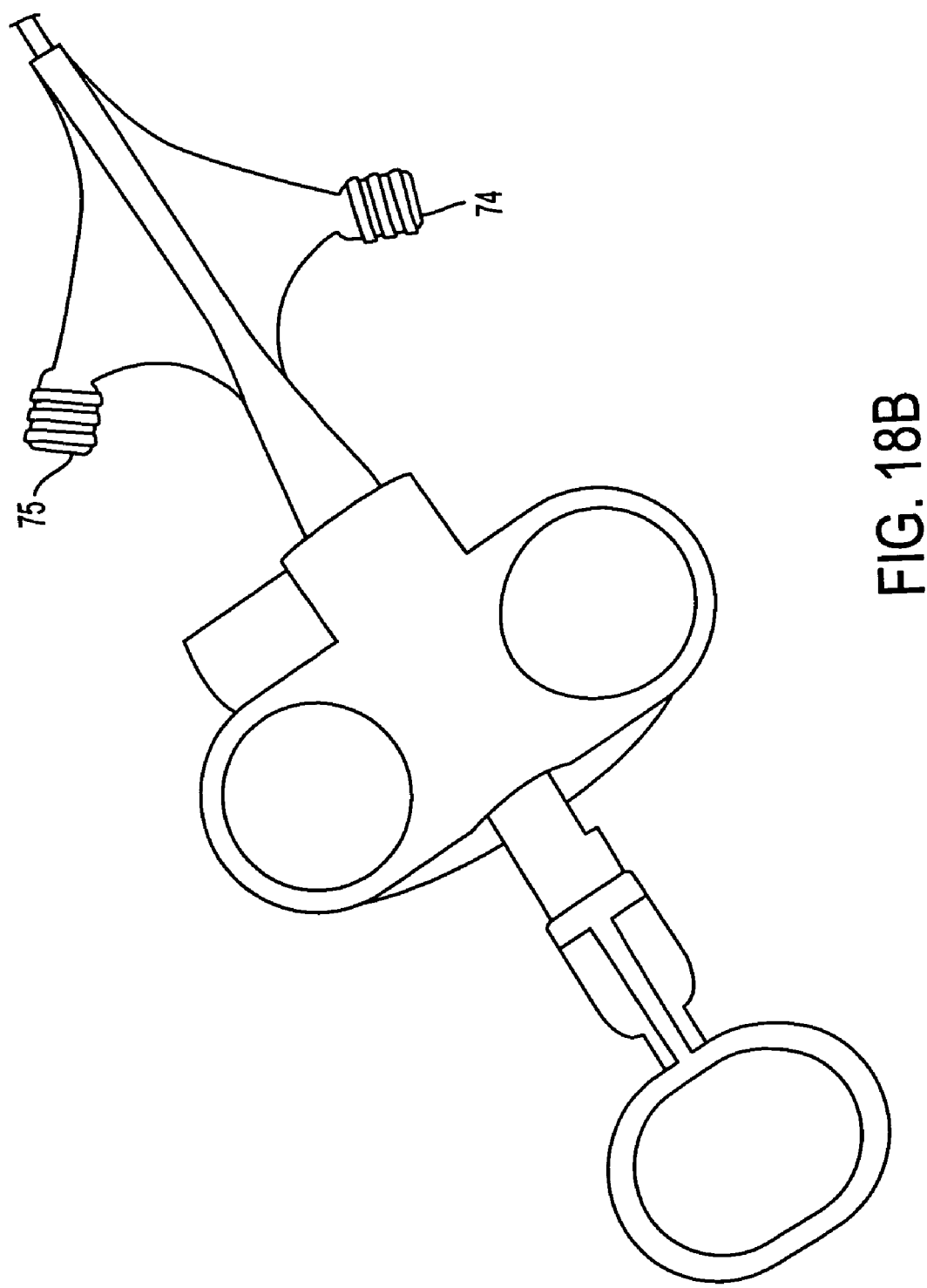

Referring to FIGS. 18a and 18b, there are several alternative means by which a bifurcation connector can be created. One of ordinary skill would understand these embodiments may be expanded from those presented in the current application.

Although the present invention is comprised of a connector with two lumens, the connector design could easily be modified to accommodate three or more lumens (FIG. 18a). This would allow future designs to incorporate both guidewire post connector 74 and injection port connector 75 into one component.

Another alternative to the bifurcation connector of the present design would be one, which also houses the electrical connector 76 (FIG. 18b). Electrical connector 76, presently incorporated into the finger ring, could be moved to the bifurcation connector.

Figure 19B:
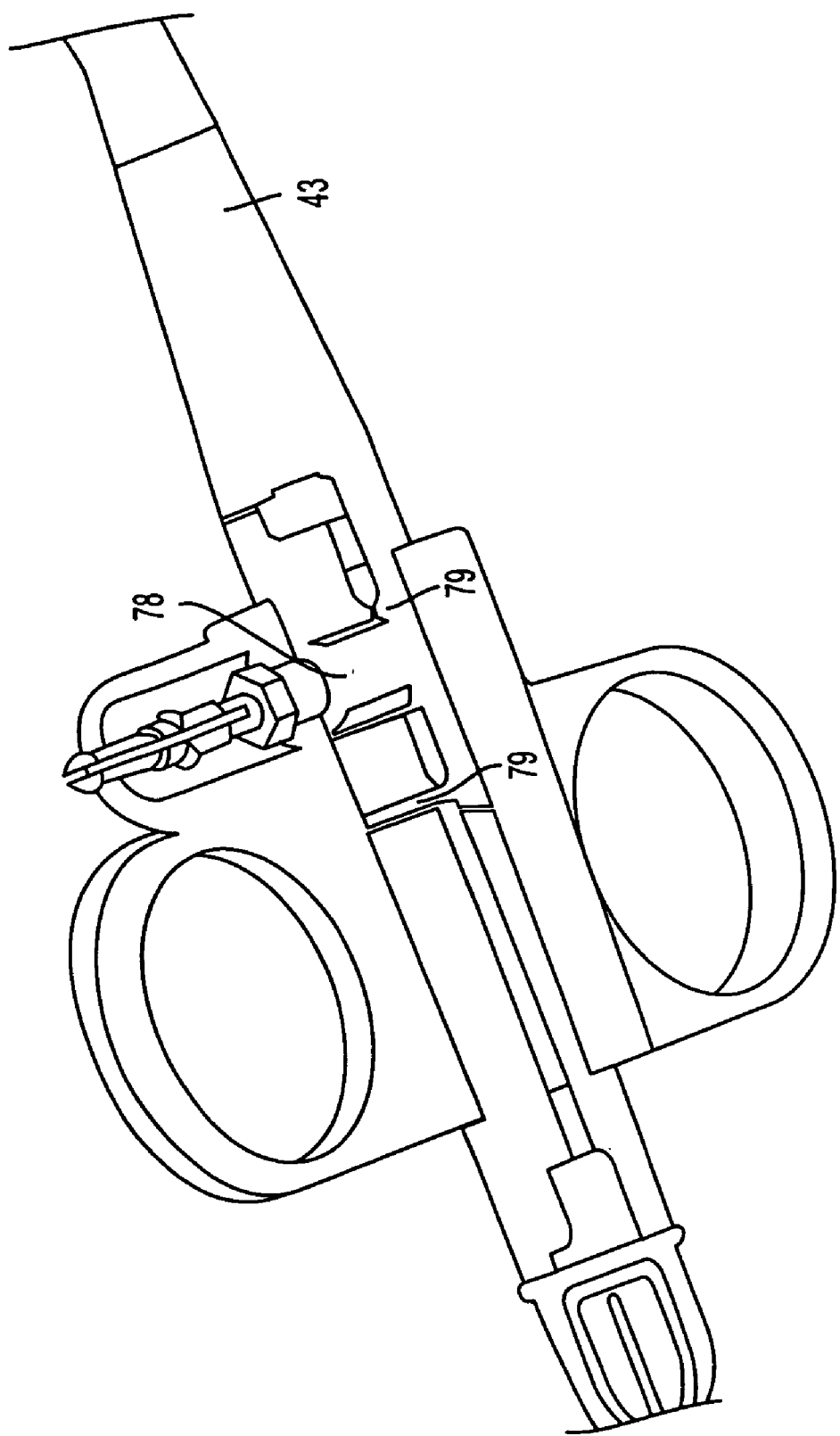
FIGS. 19a & b illustrate a bowing lock included in the present invention.

Referring now to FIGS. 19a and 19b, other embodiments of the present invention may consist of handle 66 similar to that previously described, but with the addition of a bowing lock. A bowing lock would aid the user in that handle 66 could be released at any time, and the catheter tip would maintain its bowed position. Just as the rotation lock provides for a safer and more efficient procedure, the bowing lock would do the same.

The bowing lock could be incorporated into the design in many ways. The bowing lock, in its simplest form, would consist of friction lock 77 created between finger rings 44 and main body 43 (FIG. 19a). An alternative to this design would create a similar friction lock, but would use the surfaces between wire termination 78 and main body 43 (FIG. 19b). The friction lock shown in FIG. 19b is enhanced by incorporating several lock ribs 79. Lock ribs 79 would be used to hold the catheter tip at a specific, predetermined angle. In effect, locking handle 66 into the first position would, for example, deflect the tip 30°. The next position would deflect the tip 60°. This feature would give the user even more control when positioning the catheter tip within the anatomy. In both cases, as finger rings 44 are actuated along main body 43, and catheter tip 80 is bowed, the friction between the mating components would hold the position of the handle, and thus hold the position of the bow.

The invention claimed is:

1. A method of cutting tissue in a body passage comprising selecting a catheter having a first lumen configured for receiving a wire guide, a second lumen configured for receiving an electrosurgical cutting wire, positioning said catheter in said passage at a desired position using an endoscope, actuating the electrosurgical cutting wire in the second lumen, the improvement comprising:
   orientating said electrosurgical cutting wire by rotating a handle relative to a proximal end of said catheter, said electrosurgical cutting wire also rotationally orientating a distal portion of said catheter.

2. The method of claim 1 wherein said cutting wire is affixed to said handle, wherein said step of rotating said handle causes a rotation of a proximal end of said cutting wire whereby said cutting wire is caused to rotate within said second lumen.

3. The method of claim 1 further comprising:
   inhibiting further rotation of said handle relative to said proximal end of said catheter by engaging a rotation lock.

4. The method of claim 1, further comprising:
   indicating an amount of rotation of said handle relative to said proximal end of said catheter through the use of a rotation indicator.

5. The method of claim 4, wherein said step of indicating an amount of rotation includes a visual indication of said amount of rotation.

6. A catheter handle assembly comprising:
a catheter handle;
a catheter;
a rotatable coupling connecting said catheter handle to a proximal end of said catheter, said rotatable coupling configured to allow free rotation of the proximal end of said catheter with respect to said catheter handle;
a handle clamping member affixed to said catheter handle and also affixed to a proximal end of a device, said device extending through a lumen formed in said catheter to a distal end of said catheter where said device is affixed to said catheter, whereby rotation of said catheter handle causes rotation of a proximal end of said device in said lumen, and
said rotation of a proximal end of said device causes rotational orientation of the distal end of said catheter.

7. The catheter handle assembly of claim 6, wherein said device comprises a cutting wire extending from said handle clamping member where said cutting wire is affixed to said catheter handle and said cutting wire also extending to a connection at a distal end of said catheter where said cutting wire is affixed.

8. The catheter handle assembly of claim 6, further comprising:
a rotation lock engageable to inhibit a rotation of said catheter handle with respect to said proximal end of said catheter.

9. The catheter handle assembly of claim 6, further comprising:
a rotation indicator configured to indicate an amount of rotation of said catheter handle relative to said proximal end of said catheter.

10. The catheter handle assembly of claim 9, wherein said rotation indicator comprises a visual indicator of said amount of rotation.

\* \* \* \* \*